United States Patent [19]

Manabe et al.

[11] Patent Number: 4,857,196

[45] Date of Patent: Aug. 15, 1989

[54] POROUS HOLLOW FIBER MEMBRANE AND A METHOD FOR THE REMOVAL OF A VIRUS BY USING THE SAME

[75] Inventors: Sei-ichi Manabe, Ibaraki; Masuo Satani, Moriyama, both of Japan

[73] Assignee: Asahi Kasei Kogyo Kabushiki Kaisha, Japan

[21] Appl. No.: 278,337

[22] Filed: Dec. 1, 1988

Related U.S. Application Data

[62] Division of Ser. No. 82,730, Aug. 7, 1987, Pat. No. 4,808,315.

[51] Int. Cl.⁴ ............................................. B01D 13/01
[52] U.S. Cl. .................................. 210/500.3; 514/832
[58] Field of Search ................... 210/500.23, 634, 641, 210/644, 645–647, 649, 650, 651, 652, 654, 655, 195.2, 257.2, 321.62, 321.77, 321.78, 321.8, 321.87, 321.88, 321.89; 514/832

[56] References Cited

U.S. PATENT DOCUMENTS 4,234,431 11/1980 Mishiro et al. ................. 210/500.23
4,340,481 7/1982 Mishiro et al. ................. 210/500.23
4,690,772 9/1987 Tell et al. ............................ 514/832

*Primary Examiner*—Frank Sever
*Attorney, Agent, or Firm*—Finnegan, Henderson, Farabow, Garret & Dunner

[57] ABSTRACT

There is disclosed a novel porous hollow fiber membrane which is characterized by such a unique porous structure that the inner and outer membrane surfaces have an in-a-plane average pore diameter of 0.01 to 10 μm and the porous membrane wall has an in-a-plane porosity of not less than 10% measured in every plane perpendicular to a radial direction of the annular cross-section of the hollow fiber membrane, wherein the in-a-plane porosity exhibits at least one minimum value between the inner and outer membrane surfaces. The present porous hollow fiber membrane has been found to be especially useful for the removal of a virus from an aqueous protein solution containing a virus. A virus can be effectively removed from an aqueous protein solution with not only an extremely high virus removal percentage but also an extremely high protein permeability, without causing the protein to be denatured.

9 Claims, 2 Drawing Sheets

INNER WALL SURFACE

OUTER WALL SURFACE

OUTER WALL SURFACE ← → INNER WALL SURFACE

POROUS HOLLOW FIBER MEMBRANE AND A METHOD FOR THE REMOVAL OF A VIRUS BY USING THE SAME

This is a division of application Ser. No. 07/082,730, filed Aug. 7, 1987, now U.S. Pat. No. 4,808,315.

BACKGROUND OF THE INVENTION

1. Field of the Invention

This invention relates to a porous hollow fiber membrane and a method for the removal of a virus by using the same. More particularly, the present invention is concerned with a novel porous hollow fiber membrane which is characterized by its unique porous structure wherein the inner and outer membrane surfaces have an in-a-plane average pore diameter of 0.01 to 10 $\mu$m and the porous membrane wall has an in-a-plane porosity of not less than 10% measured in every plane perpendicular to a radial direction of the annular cross-section of the hollow fiber membrane, said in-a-plane porosity exhibiting at least one minimum value between the inner and outer membrane surfaces. The present invention is also concerned with a method for the removal of a virus from an aqueous protein solution containing a virus by the use of the above-mentioned porous hollow fiber membrane. The novel hollow fiber membrane and the method of the present invention are especially useful because they are extremely effective for the removal of a virus with the great advantages that both an excellent virus removal percentage and a high filtration speed can be simultaneously attained.

2. Discussion of Related Art

Methods for the removal of viruses from aqueous solutions by using a uniform and symmetrical membrane (e.g. the microporous polyethylene hollow fiber disclosed in U.S. Pat. No. 4,401,567) are disclosed in Japanese Patent Application Laid-Open Specification Nos. 60-142860, 60-142861 and 61-168367. In these methods of prior art, hollow fiber membranes having an effective thickness of 5 $\mu$m or more and a uniform pore structure are utilized to remove viruses. As an example of such hollow fiber membranes, there can be mentioned a polyethylene microporous hollow fiber which has rectangular pores formed by microfibrils that are oriented in the lengthwise direction of the fiber and knotted portions that are connected to said microfibrils substantially at right angles thereto, the average width of the pores being in the range of from 0.05 to 0.35 $\mu$m, the pores being contiguous with each other from the inner wall surface to the outer wall surface to form a stacked, multicellular structure. In the specifications of these Japanese patent applications, there is a description to the effect that when the filtrate obtained by the filtration of HBs antigen-positive fresh human plasma using the above-mentioned hollow fiber membrane was observed by an electron microscopy, there was detected no Dane particle having a diameter of 0.042 $\mu$m. In this connection, however, it should be noted that there is no description with respect to the actual virus removal percentage (the measurable upper limit of virus removal percentage by electron microscopy is about 99%). Further, since in these cases the transmembrane pressure which is one of the filtration conditions is 50mmHg or less, and the filtration speed is extremely low, such a filtration method cannot be commercially employed for removing viruses. Furthermore, since the filtration speed is low, the physiological activity of the filtrate becomes extremely low.

On the other hand, in the Japanese Patent Application Laid-Open Specification No. 61-254202, a method is disclosed for the removal of tabaco mosaic virus from an aqueous solution containing ovalbumin by using a porous hollow fiber made of cuprammonium regenerated cellulose which has an average pore diameter of 0.02 to 0.2 $\mu$m and an in-a-plane porosity of 10% or more. However, with this method, the virus removal percentage is about 99% and the ovalbumin permeability is 43%, which is insufficient for practical use. This hollow fiber has a relatively uniform pore structure.

With the above-mentioned conventional methods in which an asymmetrical, or uniform, symmetrical porous membrane is employed, high virus removal percentage and high filtration speed (or high permeability for protein) cannot be simultaneously attained. The protein permeability of the conventional porous membranes is about 50%.

In general, if the average pore diameter of a porous membrane is decreased, the virus removal percentage is increased but the filtration speed and the protein concentration of the filtrate are lowered. If the average pore diameter is increased, the virus removal percentage is lowered to 99% or less, which is insufficient for a membrane to be used for the removal of viruses. The virus removal percentage normally required for a virus removing membrane is as high as 99.99 to 99.999999%. Thus, there has been a technical dilemma that a porous membrane cannot be simultaneously characterized by an excellent virus removal percentage and a high filtration speed when it is used for the removal of a virus from an aqueous protein solution containing a virus. Therefore, it has been desired to solve the dilemma and develop a porous hollow fiber membrane having both an excellent virus removal percentage and a high filtration speed.

SUMMARY OF THE INVENTION

With a view to developing a novel porous hollow fiber membrane free from the above-mentioned drawbacks inevitably accompanying the conventional porous membranes and a method of removing a virus, the present inventors have conducted extensive and intensive studies to attain these goals. As a result, it has unexpectedly been found that these goals can be attained by a novel porous hollow fiber membrane having a specific pore structure in which the porous polymer membrane has an in-a-plane porosity of not less than 10% measured in every plane perpendicular to a radial direction of the annular cross-section of the hollow fiber membrane and the in-a-plane porosity exhibits at least one minimum value between the inner and outer membrane surfaces.

Accordingly, it is an object of the present invention to provide a novel porous hollow fiber membrane which has an extremely high separating ability and is especially effective for removing a virus from an aqueous protein solution.

It is another object of the present invention to provide a method for removing a virus from an aqueous protein solution, which is effective not only for removing a virus with an extremely high virus removal percentage, but also for recovering a protein with a high protein permeability and without causing the protein to be denatured.

The foregoing and other objects, features and advantages of the present invention will be apparent to those skilled in the art from the following detailed description and appended claims taken in connection with the accompanying drawings.

DETAILED DESCRIPTION

Figure 1:
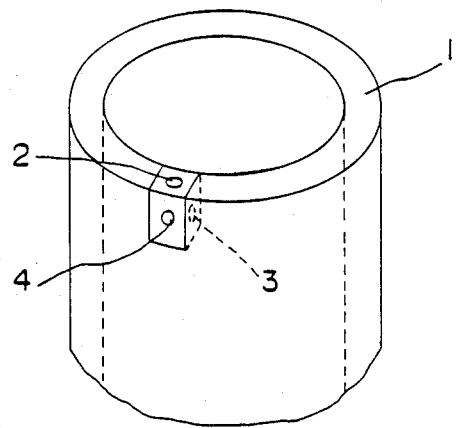
FIG. 1 is a schematic illustration of one end portion of the porous hollow fiber membrane according to the present invention, in which numeral 1 denotes the porous polymer wall of the porous hollow fiber membrane, numeral 2 denotes a portion of a transverse cross section of the porous polymer wall, numeral 3 denotes a portion of a longitudinal cross section of the porous polymer wall and numeral 4 denotes a portion of the outer wall surface of the porous hollow fiber membrane.
Figure 2:
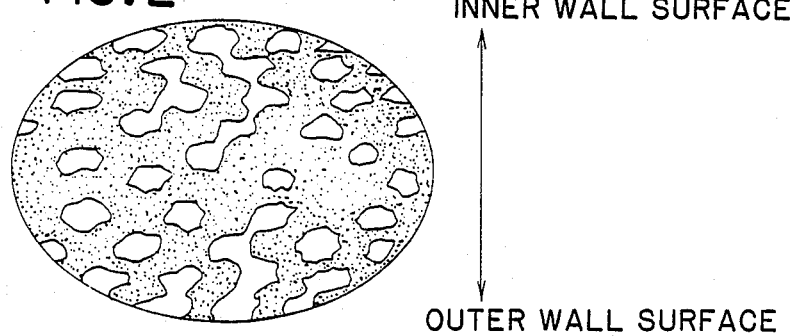
FIG. 2 is an enlarged schematic illustration of a scanning electron photomicrograph of the portion indicated by numeral 2 in FIG. 1.

In one aspect of the present invention, there is provided a porous hollow fiber membrane comprising a porous polymer wall having a substantially annular cross-section and a hollow space defined by the inner wall surface of said porous polymer wall which hollow space extends in the longitudinal direction of said porous polymer wall, said porous polymer wall having pores which form through-passages passing from the inner wall surface to the outer wall surface of said polymer wall, and wherein the inner and outer wall surfaces of said porous polymer wall have an in-a-plane average pore diameter of 0.01 to 10 μm, said in-a-plane average pore diameter being an average pore diameter as measured in a plane perpendicular to a radial direction of said annular cross-section, and said porous polymer wall has an in-a-plane porosity of not less than 10% measured in every plane perpendicular to a radial direction of said annular cross-section, said in-a-plane porosity varying continuously between said inner wall surface and said outer wall surface, wherein said in-a-plane porosity increases in the vicinity of each of said inner and outer wall surfaces and exhibits at least one minimum value between said inner and outer wall surfaces, said in-a-plane porosity at each of said inner and outer wall surfaces being at least 1.5 times the lowest value of the in-a-plane porosity within said porous polymer wall.

The most characteristic feature of the porous hollow fiber membrane of the present invention resides in that the porous hollow fiber membrane comprises a porous polymer wall having a substantially annular cross-section which membrane has a specific pore structure. The porous hollow fiber membrane of the present invention has the following pore structure characteristics:

(1) the in-a-plane average pore diameters in the inner and outer wall surfaces of the porous hollow fiber membrane as measured by scanning electron photomicrography, are in the range of from 0.01 to 10 μm;

(2) the in-a-plane porosity is not less than 10% with respect to every plane perpendicular to a radial direction of the annular cross-section;

(3) the in-a-plane porosity varies continuously between the inner wall surface of the porous hollow fiber membrane and the outer wall surface of the membrane, which porosity increases in the vicinity of each of the inner and outer wall surfaces and exhibits at least one minimum value between the inner and outer wall surfaces; and (4) the in-a-plane porosity in each of the inner and outer wall surfaces of the porous hollow fiber membrane is at least 1.5 times the lowest value of in-a-plane porosity within the porous polymer wall.

The term "in-a-plane average pore diameter" as used herein is intended to mean an average value of the pore diameters in a plane within and on the porous polymer wall, which plane is perpendicular to a radial direction of the annular cross-section of the porous polymer wall. The "plane" includes an inner and an outer wall surface of the porous polymer wall, and also includes a plane within the porous polymer wall which plane is parallel to the inner and outer wall surfaces of the porous polymer wall. Therefore, exactly stated, the plane is not flat but curved. However, since the measurement is conducted by scanning electron photomicrography with respect to an extremely limited area as will be described later, the term "plane" is used in the present invention for the sake of convenience.

Likewise, the term "in-a-plane porosity" as used herein is intended to mean a porosity in a plane within and on the porous polymer wall, which plane is perpendicular to a radial direction of the annular cross-section of the porous polymer wall. The "plane" has the same meaning as defined above.

The term "minimum value" as used herein in connection with the in-a-plane average pore diameter and the in-a-plane porosity is intended to mean a value of a varying quantity that is less than any value which immediately precedes and follows it in accordance with mathematics, and the minimum value is not necessarily equal to the lowest value. However, in a case where there is only one minimum value, the lowest value is equal to the minimum value. Likewise, the term "maximum value" as used herein in connection with the in-a-plane average diameter and the in-a-plane porosity is intended to mean a value of a varying quantity that is greater than any value which immediately precedes and follows it in accordance with mathematics, and the maximum value is not necessarily equal to the highest value.

Figure 3:
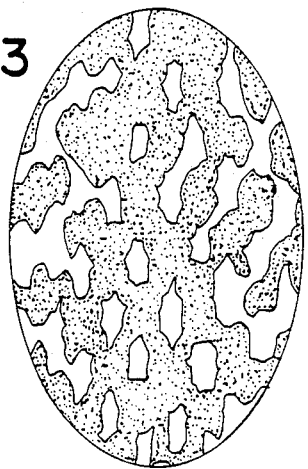
FIG. 3 is an enlarged schematic illustration of a scanning electron photomicrograph of the portion indicated by numeral 3 in FIG. 1.
Figure 4:
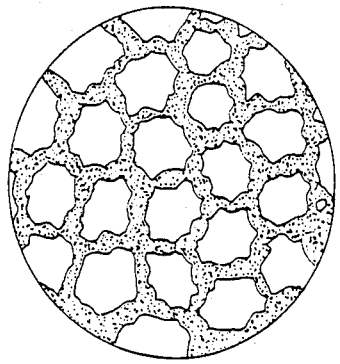
FIG. 4 is an enlarged schematic illustration of a scanning electron photomicrograph of the portion indicated by numeral 4 in FIG. 1.

Referring now to FIGS. 1 to 4, there is shown schematic illustrations for the purpose of illustrating the specific pore structure of the porous hollow fiber membrane. In FIG. 1, numeral 1 denotes the porous polymer wall of the porous hollow fiber membrane, numeral 2 denotes a portion of a transverse cross section of the porous polymer wall, numeral 3 denotes a portion of a longitudinal cross section of the porous polymer wall and numeral 4 denotes a portion of the outer wall surface of the porous hollow fiber membrane In, FIG. 2, there is shown an enlarged schematic illustration of a scanning electron photomicrograph of the portion indicated by numeral 2 in FIG. 1. In FIG. 3, there is shown an enlarged schematic illustration of a scanning electron photomicrograph of the portion indicated by numeral 3 in FIG. 1. In FIG. 4, there is shown an enlarged schematic illustration of a scanning electron photomicrograph of the portion indicated by numeral 4 in FIG. 1. As is apparent from FIGS. 2 to 4, pores (vacant portions) are uniformly present in the surface of the porous polymer wall, but non-uniformly present in the thicknesswise direction of the porous polymer wall. That is, the in-a-plane porosity varies continuously between the inner wall surface and the outer wall surface. Further, the in-a-plane porosity increases in the vicinity of each of the inner and outer wall surfaces toward a value of the in-a-plane porosity at each of the inner and outer wall surfaces, and exhibits at least one minimum value between the inner and outer wall surfaces. The in-a-plane porosity at each of the inner and outer wall surfaces is at least 1.5 times the lowest value of the in-a-plane porosity within the porous polymer wall. The pore characteristics as mentioned just above will be more clearly understood from FIG. 5.

Figure 5:
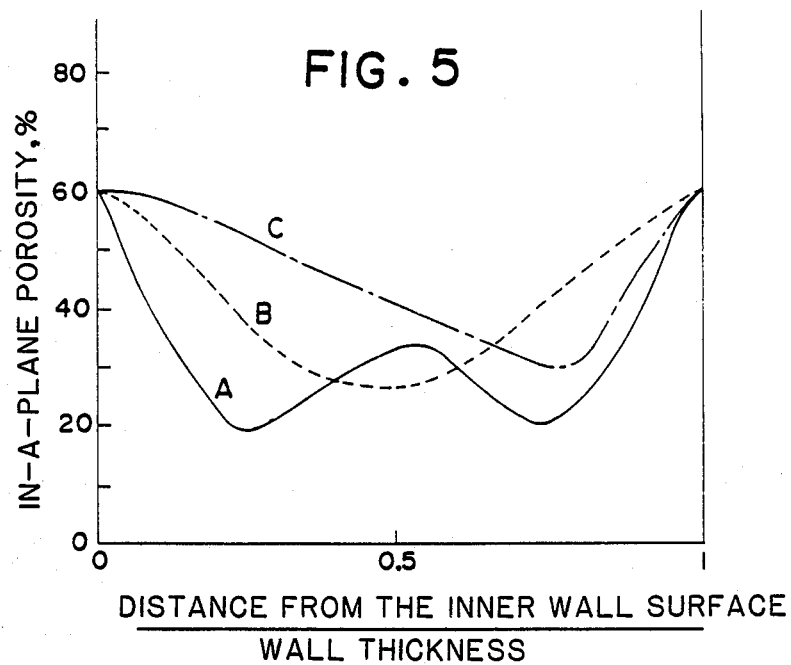
FIG. 5 is a graph showing the variation of the in-a-plane porosity with the variation of the distance of the plane from the inner wall surface with respect to various types of porous hollow fiber membranes according to the present invention.

In FIG. 5, there is shown a graph showing the variation of the in-a-plane porosity with the variation of the distance of the plane from the inner wall surface (hereinafter often referred to simply as "variation of the in-a-plane porosity") with respect to various types of porous hollow fiber membranes according to the present invention. Curve A indicates the variation of the in-a-plane porosity with respect to a porous hollow fiber having two minimum values of the in-a-plane porosity. Curve B indicates the variation of the in-a-plane porosity with respect to the porous hollow fiber of Example 1 (given later), which has one minimum value of the in-a-plane porosity at a middle portion between the inner and outer wall surfaces. Curve C indicates the variation of the in-a-plane porosity with respect to a porous hollow fiber which is similar to the porous hollow fiber of Curve B in that both the hollow fibers of Curve C and Curve B have one minimum value of the in-a-plane porosity. However, the hollow fiber of Curve C is similar to that of Curve A in the virus-removing effect because both of these hollow fibers have a minimum value of the in-a-plane porosity in a portion deviated from the middle portion to the side of the outer wall surface. Curve A corresponds to a porous hollow fiber membrane in which there are two occurrences of minimum values of the in-a-plane porosity and those minimum values are in the range of from about 10% to about 20%, i.e. the minimum values are small. In such a hollow fiber membrane, in the portions at which the in-a-plane porosity is at a minimum, the in-a-plane average pore diameter is likely to be extremely small as compared to those in the inner and outer wall surfaces, that is, a skin construction is likely to be formed. Therefore, although such a hollow fiber membrane has a slightly low protein permeability (for instance, about 70%), the hollow fiber membrane is preferably used for the removal of viruses in which the virus removal percentage is required to be especially high (for instance, more than 99.999999%).

Porous hollow fiber membranes having various in-a-plane porosity variations can be obtained by controlling various conditions in the process of producing the porous hollow fiber membrane, that is, they can be obtained by controlling the compositions of the injection liquid and the coagulating bath, the period of time for which the spinning solution is in contact with the injection liquid and the coagulating bath and the like.

The minimum value of the in-a-plane porosity can be mathematically determined on the basis of the curve as obtained by dividing the membrane wall into 10 sections in the radial direction from the inner wall surface of the membrane to the outer wall surface of the membrane and plotting the value of the in-a-plane porosity, as measured by the method described later, at each of the points against $Z/d$, in which $Z$ represents the distance from the inner wall surface and $d$ represents the thickness of the membrane (see FIG. 5).

The porous hollow fiber membrane is made mainly of a polymer. Examples of a polymer include homopolymers and copolymers of acrylonitrile, sulfone, vinylidene chloride, vinyl chloride, vinyl acetate, methyl methacrylate, urethane, styrene and vinyl alcohol; polytrifluorochloroethylene; polytetrafluoroethylene; polyolefins such as polyethylene and polypropylene; polyamides; polyesters; cellulose acetate, cellulose nitrate, cellulose butyrate and cellulose acetate butyrate; regenerated cellulose; and cellulose and mucopolysaccharides. The composition of the porous polymer wall of the hollow fiber membrane may comprise 50% by weight or more of a polymer and 50% by weight or less of a suitable additive, for example, inorganic low molecular weight compounds such as silica and activated carbon, and organic low molecular weight compounds such as plasticizers and surfactants.

A preferred process for producing the porous hollow fiber is now described as follows. In the process, a spinning solution of a polymer is extruded through an annular orifice to form a fiber extrudate with a hollow space while simultaneously injecting an injection liquid into the hollow space of the fiber extrudate through an injection tube provided in the center of the annular orifice. In this instance, the fiber extrudate should be immediately immersed into the coagulating liquid. During the above-mentioned process, there occurs a microphase separation in the wall of the fiber extrudate by the action of both the injection liquid and the coagulating liquid. The microphase separation initially occurs at the inner and outer wall surfaces of the fiber extrudate and progresses into the interior of the wall. The term "microphase separation" as used herein means a state wherein a polymer-rich phase or a polymer-lean phase is stably dispersed as particles having a diameter of about 0.01 to about 5 $\mu$m in a polymer solution. Due to the formation of the particles, the polymer solution first loses its transparency, and then gradually undergoes coagulation and regeneration. The resultant porous membrane has such a characteristic structure that the surface of a frozen fracture of the porous membrane consists of many particles linked together having a diameter in the range of from 0.1 to several $\mu$m see FIGS. 2 and 3).

In producing the porous hollow fiber membrane of the present invention, it is necessary that the spinning solution be free from bubbles and undissolved residues, that the composition of the spinning solution be strictly controlled and the temperature of the spinning solution be maintained strictly at 10° to 40° C., desirably at a temperature near the ambient temperature, and that the injection liquid delivered from the injection tube disposed in the center of the orifice and the coagulating liquid have the same or similar strictly controlled composition, and the temperature thereof be maintained at 10° to 40° C., desirably at a temperature near the ambient temperature. The process of producing the porous hollow fiber membrane of the present invention will be further illustrated, taking an example in which a cuprammonium regenerated cellulose solution is used as a polymer. The porous hollow fiber membranes of the present invention using other polymers can also be produced in substantially the same manner as described below.

Cellulose linters are dissolved in a cuprammonium solution so that the cellulose concentration becomes from 2 to 10% by weight, to obtain a spinning solution. The spinning solution must be homogeneous and completely filtered and deaerated, and the cellulose concentration must be maintained at a predetermined level within ±0.05% by weight during the spinning. It should be ensured that the filtration of the spinning solution is complete and, therefore, no impurities and undissolved cellulose are contained in it. The temperature of the spinning solution is maintained at a predetermined point within ±0.1° C., and the temperature of the atmosphere of the spinning machine is controlled so as not to cause unevenness in the temperature of the spinning solution. Mainly by changing the cellulose concentration of the spinning solution, the in-a-plane porosity and in-a-plane average pore diameter in the inner and outer wall surfaces of the porous hollow fiber membrane can be changed. The thus prepared spinning solution is allowed to be extruded from the orifice (e.g. 2 mm in diameter) at a fixed rate (e.g. 1.0 to 5.0 ml/min). In this instance, it should be ensured that undulation is not caused. Simultaneously with the extrusion of the spinning solution, a solution which causes microphase separation to the spinning solution (e.g. a ternary system consisting of acetone, ammonia and water in a ratio such as 35:1:50) as an injection liquid is injected from the injection tube (e.g. 0.6 mm in diameter) at a fixed rate (e.g. 2.0 to 20 ml/min). The composition and the temperature of the injection liquid are required to be controlled at least as strictly as those of the spinning solution. In this connection, by changing the composition of the injection liquid, not only the in-a-plane porosity and in-a-plane average pore diameter in the inner wall surface but also those within the wall can be changed. The fiber shaped extrudate (the inner part is the injection liquid and the outer part is the spinning solution) is immediately immersed into the coagulating bath. The composition of the coagulating liquid (a ternary system consisting of e.g. acetone, ammonia and water) is formulated to be identical or similar to that of the injection liquid, and the composition and the temperature must be controlled as strictly as those of the injection liquid. By changing the composition of the coagulating liquid, not only the in-a-plane porosity and in-a-plane average pore diameter in the outer wall surface but also those within the wall can be changed. The depth of the coagulating bath and the take-up speed is set so that the fiber-shaped extrudate is immersed in the coagulating bath for a fixed period of time (e.g. 1 to 30 min). After being taken up, the resultant fiber is subjected to regeneration using an aqueous sulphuric acid solution having a concentration of 2% by weight, followed by water washing and drying.

The porous hollow fiber membrane of the present invention is capable of completely removing the viruses contained in an aqueous protein solution even when the membrane has in-a-plane average pore diameters larger than the diameter of the viruses in the inner and outer wall surfaces of the membrane, due to the above-mentioned pore structure characteristics of items (1) to (4) above of the membrane. The porous hollow fiber membrane of the present invention is highly effective in inhibiting the passage of viruses therethrough due to the pore characteristic change in a radial direction of the annular cross-section of the membrane wall and to the presence of a minimum value of the in-a-plane porosity at least at one portion between the inner and outer wall surfaces as mentioned in item (3) above. Moreover, the porous hollow fiber membrane of the present invention does not adversely affect the permeation of proteins therethrough due to the pore structure characteristics as mentioned in items (1), (2) and (4) above. Therefore, in removing a virus from an aqueous protein solution, the physiological activity of the protein recovered using the porous hollow fiber membrane of the present invention is extremely excellent as compared with the physiological activity of the protein recovered by the conventional methods.

The protein permeability and protein permeation rate of the present porous hollow fiber membrane can be improved by causing the porosity of one surface of the membrane from which a protein is permeated to become larger than that within the membrane wall. For example, no matter what kind of polymer is employed as the wall material of the membrane, the value of $V_A/V_W$, in which $V_A$ represents the permeability for an aqueous 5% by weight albumin solution and $V_W$ represents the permeability for purified water, is significantly improved when the ratio of the in-a-plane porosity in one surface of the membrane, from which permeation of the water and albumin solution is performed, to the lowest value of the in-a-plane porosities within the membrane wall, is at least 1.5, as compared with that when such ratio is 1. The value of $V_A/V_W$ is remarkably improved, and sometimes becomes twofold or more, when the above-mentioned ratio is at least 2.

From the viewpoint of further improving the capability of inhibiting the passage of viruses through the membrane, it is preferred that the porous polymer wall have a pore structure in which the in-a-plane average pore diameter varies continuously between the inner wall surface and the outer wall surface so that from the inner wall surface toward the outer wall surface, the in-a-plane average pore diameter alternately decreases and increases at least two times, thereby experiencing occurrences of at least a minimum value, a maximum value and a minimum value, in this order, in the continuous variation of the in-a-plane average pore diameter between the inner and outer wall surfaces, wherein the in-a-plane average pore diameter increases in the vicinity of said outer wall surface and in which the wall portion of the membrane has a layer structure as described later. With the last increase in the above-mentioned alternate decrease and increase of the in-a-plane average pore diameter, the in-a-plane average pore diameter increases toward a value of the in-a-plane average pore diameter at the outer wall surface.

The in-a-plane average pore diameter within the porous polymer wall is in the range of 0.005 to 10 μm.

The in-a-plane average pore diameter at a plane exhibiting a minimum in-a-plane porosity value with respect to the porous hollow fiber membrane of the present invention may be larger than the diameters of the viruses to be removed. Generally, when the number of layers constituting the layer structure of the wall portion of the present porous hollow fiber membrane is large, even if the in-a-plane average pore diameter at the plane exhibiting a minimum in-a-plane porosity value is about twice the diameters of the viruses, the membrane is capable of highly effectively inhibiting the passage of the viruses therethrough. The porous hollow fiber membrane of the present invention may advantageously have a layer structure in the direction of the wall thickness, so that the membrane has the following characteristics:

(1) uniformity in pore characteristics such as pore diameter distribution and pore configuration is observed at any portion of any particular plane which is in parallel with the inner and outer wall surfaces, and any of such planes is approximated to a screen filter in the light of filtering properties;

(2) in any particular plane which is in parallel with the inner and outer wall surfaces, the pores are randomly disposed or regularly arranged only along the direction of the fiber axis;

(3) the specific pore diameter distribution, in-a-plane average pore diameter and in-a-plane porosity are measurable with respect to any of such planes;

(4) each of such planes has a different pore diameter distribution, different average pore diameter and different in-a-plane porosity, depending on the distance, in a radial direction of the annular cross-section of the membrane wall, of the plane from the inner wall surface of the membrane. In the light of the principle governing the formation of the present porous hollow fiber membrane, the above-mentioned planes are each approximated to a section of a layer having a thickness of formula $$\frac{2}{\sqrt{6}} \times (2S_2)$$

wherein $2S_2$ represents the diameter of fine particles formed by the microphase separation as described hereinbefore, which section is in parallel with the surface of the layer. It is preferred that the number of layers constituting the porous polymer wall of the porous hollow fiber membrane of the present invention be in the range of from about 10 to about 300. The number of layers is preferably not larger than about 300 from the viewpoint of ensuring high permeability for proteins or the like. The "number of layers" as used herein is defined as $\sqrt{6}\, d/4S_2$ in which d represents the wall thickness of the membrane and $S_2$ is as defined above. On the other hand, a plane perpendicular to the fiber axis which plane is represented by the cross section of the porous hollow fiber membrane is approximated to a layer-form accumulation of particles having a diameter of from 0.1 to 2 $\mu$m.

To improve the capability of inhibiting the passage of viruses through the membrane, it is preferred that the average shear rate of the filtrand flow on the inner wall surface of the hollow fiber be increased. For example, when the shear rate is 1000 sec$^{-1}$ or more, the capability of inhibiting the passage of viruses is about 10 times that exhibited when it is 0.

The ratio of the maximum value of the in-a-plane average pore diameter to the minimum value of the in-a-plane average pore diameter with respect to the porous hollow fiber membrane of the present invention is preferably in the range of from 1.2 to 10, more preferably from 1.2 to 2. The presence of a maximum value with respect to the in-a-plane average pore diameter is desirable from the viewpoint of increasing the filtration rate of an aqueous protein solution. It is also desirable from the viewpoint of improving the mechanical property of the hollow fiber membrane since it provides a cushion against a mechanical deformation of the hollow fiber membrane. However, when the maximum value of in-a-plane average pore diameter is too large, the capability of the membrane of inhibiting the passage of viruses therethrough tends to become poor. For this reason, the above-mentioned ratio of the maximum value of in-a-plane average pore diameter to the minimum value of in-a-plane average pore diameter is preferably 10 or less, more preferably 2 or less.

The upper limit of the in-a-plane porosity with respect to the porous hollow fiber according to the present invention is not limited but may preferably be about 80% from the viewpoint of ease of production of the membrane.

The hollow fiber membrane of the present invention preferably has a wall thickness of from 10 $\mu$m to 200 $\mu$m. If a membrane having a wall thickness of less than 10 $\mu$m is employed, the virus removal percentage is lowered. On the other hand, if a membrane having a wall thickness of more than 200 $\mu$m is employed, the protein permeability decreases, leading to a lowering of the recovery of protein.

· The bulk porosity of the hollow fiber membrane of the present invention is preferably 30 to about 75%, more preferably 40 to about 75%. As the bulk porosity increases, the permeation rate of protein increases. The ratio of the increase in the permeation rate of protein to the increase in the bulk porosity becomes large as the bulk porosity becomes 30% or more and this ratio becomes even larger as the bulk porosity becomes 40% or more. On the other hand, if the bulk porosity is more than about 75%, the performance of the membrane with respect to the removal of viruses becomes poor.

The number of pores which are present in each of the porous inner and outer surfaces of the polymer wall of the porous hollow fiber membrane of the present invention is preferably $10^6/\text{cm}^2$ or more.

The apparent average pore diameter in the porous polymer wall is in the range of 14 to 150 nm.

If the liquid to be subjected to the removal of viruses has a protein concentration of 3% or more, adsorption of the protein onto the polymer constituting the membrane has a large effect on the permeability of protein, recovery thereof and filtration rate. In this connection, it is noted that a membrane made of a hydrophilic polymer has a large value of $V_A/V_W$ in which $V_A$ and $V_W$ are as defined above and, hence, preferable. Further, with respect to porous hollow fiber membranes having substantially the same in-a-plane porosities and in-a-plane average pore diameters at the inner and outer wall surfaces, a porous hollow fiber membrane produced by a microphase separation method has a higher filtration rate and a higher filtration capacity than porous hollow fiber membranes produced by other methods such as a method in which a substance having a low molecular weight is emulsified and mixed with a polymer solution to obtain a spinning solution, the obtained solution is spun into a hollow fiber and then the substance having a low molecular weight is removed from the hollow fiber. Therefore, a porous hollow fiber membrane produced from a hydrophilic polymer by a microphase separation method is preferably used for removing viruses from an aqueous protein solution having a high protein concentration.

Blood plasma is an example of an aqueous protein solution which may be subjected to the removal of viruses according to the method of the present invention. In the removal of viruses from blood plasma, which has a protein concentration of 5% or more, the chemical structure of the polymer constituting the porous hollow fiber membrane has a large effect on the performance of the membrane. In this connection, a membrane made of a polymer containing a large number of hydroxy groups, such as a regenerated cellulose, is preferable from the viewpoints of the filtration capacity of the membrane and the recovery of proteins. A membrane produced from a cuprammonium regenerated cellulose by a microphase separation method is especially preferable.

Viruses in human blood plasma, for example, hepatitis virus, AIDS (acquired immune deficiency syndrome) virus, etc., are generally highly infectious to human beings and have a serious effect on human bodies after infection. Therefore, in the removal of these viruses from human blood plasma, the removal percentage is required to be 99.999% to 99.999999%. For removing viruses with such a high removal percentage, there may preferably be used a porous hollow fiber membrane, wherein the membrane has a layer structure consisting of 10 or more layers and the ratio of the minimum value of the in-a-plane porosity (%) to the value of the wall thickness ($\mu$m) is in the range of from 0.05 to 2.0. Of the above-mentioned membrane, a membrane having a layer structure consisting of 100 or more layers is more preferable.

In another aspect of the present invention, there is provided a method for the removal of a virus contained in an aqueous protein solution, which comprises contacting an aqueous protein solution containing a virus with a porous hollow fiber membrane comprising a porous polymer wall having a substantially annular cross-section and a hollow space defined by the inner wall surface of said porous polymer wall which hollow space extends in the longitudinal direction of said porous polymer wall, said porous polymer wall having pores which form through-passages passing from the inner wall surface to the outer wall surface of said polymer wall, and wherein the inner and outer wall surfaces of said porous polymer wall have an in-a-plane average pore diameter of 0.01 to 10 $\mu$m said in-a-plane average pore diameter being an average pore diameter as measured in a plane perpendicular to a radial direction of said annular cross-section, and said porous polymer wall has an in-a-plane porosity of not less than 10% measured in every plane perpendicular to a radial direction of said annular cross-section, said in-a-plane porosity varying continuously between said inner wall surface and said outer wall surface, wherein said in-a-plane porosity increases in the vicinity of each of said inner and outer wall surfaces and exhibits at least one minimum value between said inner and outer wall surfaces, said in-a-plane porosity at each of said inner and outer wall surfaces being at least 1.5 the lowest value of the in-a-plane porosity within said porous polymer wall, said contacting of the solution with the membrane being conducted on either of the inner and outer wall surfaces of the porous polymer wall while applying a trans-membrane pressure, thereby causing the virus contained in the aqueous protein solution to be captured in the porous hollow fiber membrane while allowing the aqueous protein solution to permeate through the porous hollow fiber membrane.

The method of the present invention can be suitably applied to a virus-containing aqueous protein solution such as plasma, particularly human plasma, or the like. The aqueous protein solution to be treated by the method of the present invention has a protein concentration of 0.5 to 30% by weight in terms of total protein concentration which protein is part of useful components of the solution. As examples of such aqueous protein solutions, there may be mentioned human or animal blood or plasma, materials and intermediates for plasma derivatives, aqueous solutions containing plasma derivatives, growth hormone, injections containing physiologically active substances such as growth hormone, vaccine and the like, cell culture fluid, aqueous product solutions in the fermentation industry and intermediates therefor, diagnostics, serums for cell culturing, vaccine and the like. As viruses to be removed by the method of the present invention, there may be mentioned hepatitis virus, AIDS virus, influenza virus, poliomyelitis virus and the like which are pathogenic to human beings and/or animals.

In the method of the present invention, an aqueous protein solution containing a virus is contacted with either the inner wall surface or the outer wall surface of the porous hollow fiber membrane. The contact of the aqueous protein solution with the wall surface of the porous hollow fiber membrane may be effected either by flowing the solution along the wall surface or by applying the solution in the stationary state onto the wall surface. In the ultrafiltration involved in the method of the present invention, a trans-membrane pressure of about 0.1 to 1 atm is applied.

By the method of the present invention, the virus is effectively captured in the porous hollow fiber membrane and, thus, can be removed from the aqueous protein solution, not only with an extremely high virus removal percentage but also with a high protein permeability. Therefore, the high filtration speed is realized. Further, it should be noted that according to the method of the present invention, the protein contained in the aqueous protein solution is not denatured and there is no danger that the biological activity of the protein is lowered.

Figure 6:
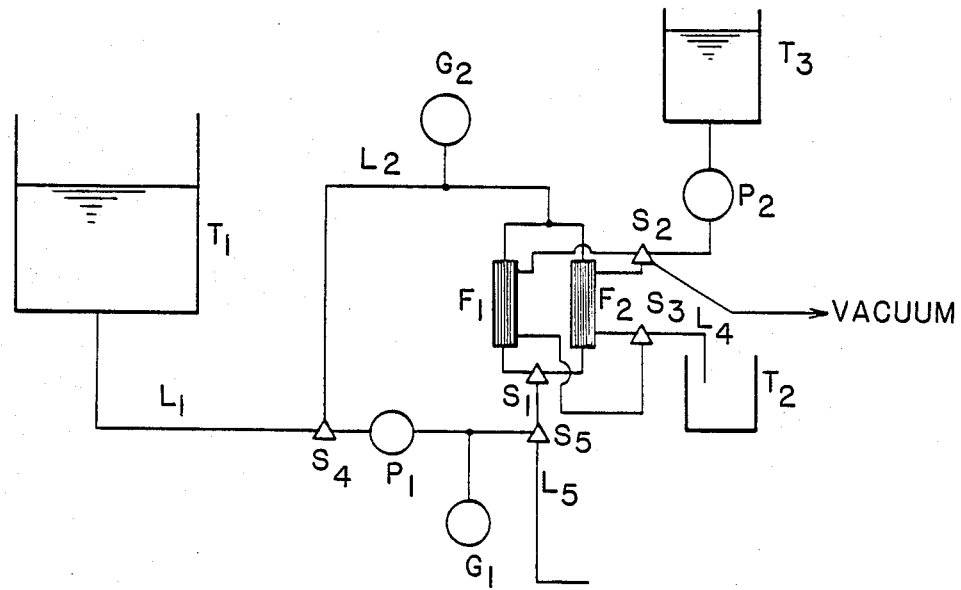
FIG. 6 is a flow diagram illustrating one mode of the method of the present invention in which viruses are removed from an aqueous protein solution.

Referring to FIG. 6, there is a flow diagram illustrating one mode of the present invention in which viruses are removed from an aqueous protein. A plurality (about 10,000) of the porous hollow fiber membranes of the present invention are bundled to obtain a module. Two modules are designated by $F_1$ and $F_2$. Plasma obtained from a plurality of persons is pooled in a tank $T_1$. The temperature of the plasma is maintained at about 4° C. The plasma is supplied to the module $F_1$ or $F_2$ through a line L1 by the manipulation of switches $S_4$, $S_5$ and $S_1$ at a predetermined flow rate by a pump $P_1$ (in this case, the plasma is flowed into the hollow space of the hollow fiber membrane). The amount of the pressure applied to the module $F_1$ or $F_2$ is given as the difference between the pressure values at an entry port side pressure gage $G_1$ and an outlet side pressure gage $G_2$ and a vacuum line. By manipulating the switch $S_1$, the module $F_1$ or $F_2$ is selected. A filtrate from the module $F_1$ or $F_2$ flows to a tank $T_2$ through a line L4 by the manipulation of a switch $S_3$. Any residual filtrand flows through a line L2, and, by the manipulation of the switch $S_4$, is then supplied to the module $F_1$ or $F_2$ again by the pump $P_1$.

By the manipulation of a switch $S_2$ and the operation of a pump $P_2$, the module $F_1$ or $F_2$ is back washed by a buffer solution stored in a tank $T_3$. The initial part of the liquid flowing back into the hollow space of the hollow fiber membranes by the back-washing enters the line $L_2$, and the latter part of the liquid is led out of the system through a line $L_5$ by the manipulation of switches $S_1$ and $S_5$. By this procedure, not only the back-washing of the hollow fibers is conducted, but also an excessive increase in the protein concentration within the line $L_2$ is prevented, thereby enabling the filtration speed in the module $F_1$ and $F_2$ to be stably maintained, so that the recovery of a virus-free protein solution can be attained with high efficiency.

As applications of the method of the present invention, there may be mentioned (1) separation of viruses from human plasma (production of plasma for transfusion), (2) removal of viruses from pooled plasma or plasma preparations (production of plasma preparations), (3) removal of viruses from drugs and aqueous solutions used in genetic engineering, (4) removal of viruses from a cell culture fluid, (5) removal of viruses from reagents for clinical laboratory tests, (6) removal of viruses from injection reagents, (7) and removal of unneeded viruses in the production process of vaccine, or concentration of viruses. Thus, the present invention can be advantageously utilized in fields such as medicine, biochemistry, animal husbandry and the like.

In the Examples, the in-a-plane average pore diameter, the in-a-plane porosity, the bulk porosity and the apparent average pore diameter were measured by the following methods.

(1) In-a-plane average pore diameter ($2\bar{r}$) and in-a-plane porosity (Pre)

Water in the interior of a porous hollow fiber membrane in the wet state is replaced by a water-soluble organic solvent such as acetone and the hollow fiber membrane is subjected to air-drying. After drying, the hollow fiber membrane is embedded in a polymer resin such as an acrylic resin to obtain a resin-embedded hollow fiber. Using an ultramicrotome (Ultratome III 8800 type manufactured and sold by LKB Ltd., Sweden) equipped with a glass knife, sections which are perpendicular to a radial direction of the hollow fiber and have a thickness of about 1 μm in the radial direction are cut out from the resin-embedded hollow fiber, at a plurality of predetermined distances from the inner wall surface in the radial direction. Then, the resin used for the embedment of the hollow fiber is dissolved out from the sections with a solvent such as chloroform. Thereafter, an electron micrograph of each section is taken.

The in-a-plane average pore diameter ($2\bar{r}$) with respect to a plane in the polymer wall of the hollow fiber is represented by the formula $$2\bar{r} = 2\sqrt{\bar{r}_3 \cdot \bar{r}_4}$$

wherein $\bar{r}_3$ and $\bar{r}_4$ are respectively represented by the formulae $$\bar{r}_3 = \frac{\int_0^\infty r^3 N(r) dr}{\int_0^\infty r^2 N(r) dr}$$

$$\bar{r}_4 = \frac{\int_0^\infty r^4 N(r) dr}{\int_0^\infty r^3 N(r) dr}$$

in which
r is the pore radius on the surface of the section corresponding to the plane; and
N(r) is a pore radius distribution function defined on the basis that the number of pores having a pore radius falling within the range of r to r+dr per 1 cm² area of the surface of the section is expressed as N(r)dr.

The pore radius distribution function [N(r)] is determined by the electron photomicrograph of the section as follows. With respect to the area of the section of which the pore radius distribution function is to be determined, a scanning electron photomicrograph is taken and an enlarged print thereof having an appropriate size (for instance 20 cm×20 cm) is made. On the thus obtained print, 40 straight test lines are drawn at an equal interval. Each line crosses over a number of pores. With respect to every pores which have been crossed over by a straight test line, the length of the portion of the straight line which lies within the pore is measured. Using the frequency distribution function with respect to the length thus measured, N(r) is determined by, for example, the method of stereology [see, for example, Norio Suwa, "Teiryo Keitaigaku (Quantitative morphology)" (published by Iwanami Shoten, Japan), p. 185-272].

The in-a-plane porosity (Pre) with respect to a plane in the polymer wall of the hollow fiber is obtained by calculation from the following formula $$Pre\ (\%) = \left\{ \pi \int_0^\infty r^2 N(r) dr \right\} \times 100$$

wherein r and N(r) are as defined above. The pore radius distribution [N(r)] is determined in the same manner as mentioned above.

(2) Bulk porosity (Prp)

Water in the interior of a porous hollow fiber membrane in the wet state is replaced by a water-soluble organic solvent such as acetone and the hollow fiber membrane is subjected to air-drying. After the air-drying, the hollow fiber membrane is further dried in vacuo to reduce the moisture content of the membrane to 0.5% or less. The bulk porosity of the membrane is obtained by calculation from the following formula $$P_{rp}\ (\%) = \left\{ 1 - \frac{W}{\rho/4 \times \pi(R_0^2 - R_1^2) \times l} \right\} \times 100$$

wherein
Ri, Ro, l and W respectively represent the inner diameter (cm), outer diameter (cm), length (cm) and weight (g) of the hollow fiber after drying in vacuo; and
$\rho$ is the density of the polymer constituting the porous hollow fiber.

(3) Apparent average pore diameter ($2\bar{r}_f$)

Water is applied to the inner wall surface of a porous hollow fiber at a predetermined transmembrane pressure $\Delta P$ (cm Hg). The filtration flux J (ml/cm$^2$/sec) is obtained. The apparent average pore diameter ($2\bar{r}_f$) can be obtained by calculation based on the following formula derived from Poiseuille's equation $$2\bar{r}_f(cm) = 4.6 \times 10^{-2} (\eta Jd/\pi P_{rp} \Delta P)^{\frac{1}{2}}$$

wherein:
d is the wall thickness (cm) of the porous hollow fiber membrane;
$\eta$ is the viscosity coefficient (centipoise);
$P_{rp}$ is the bulk porosity of the porous hollow fiber membrane (%); and
J and $\Delta P$ are as defined above.

The present invention will now be described in detail with reference to the following Examples, which should not be construed to limit the scope of the present invention.

EXAMPLE 1

Cellulose linter having a viscosity average molecular weight of $1.50 \times 10^5$ was prepared according to a customary known method. The prepared cellulose linter was dissolved in an aqueous cuprammonium solution having ammonia and copper concentrations of 6.8% by weight and 3.1% by weight, respectively, so that the final concentration of the cellulose linter in the resulting cellulose linter solution became 7.0% by weight. Then, the cellulose linter solution was filtered, followed by degassing, thereby to obtain a spinning solution. The spinning solution was extruded through a spinneret having an orifice diameter of 2 mm, an injection-tube outside diameter of 0.8 mm and an injection-tube inside diameter of 0.6 mm at a delivery rate of 2.0 ml/min to form a fiber extrudate with a bore, while simultaneously injecting an injection liquid through the injection tube disposed in the center of the orifice into the bore at a delivery rate of 5.0 ml/min. During this procedure, both the spinning solution and injection liquid were maintained at 25°±0.1° C. As the injection liquid, a solution whose composition was strictly controlled so that the proportions of water, acetone and ammonia were 100.0:70.0:1.0 by weight was employed. The fiber extrudate was immediately introduced into a coagulating bath maintained at a temperature of 25°±0.1° C. whose composition was strictly controlled so that the proportions of water, acetone and ammonia were 100.0:70.0:1.0 by weight, followed by reeling up at a velocity of 7.0 m/min from the bath. In the coagulating bath, the fiber extrudate which had been transparent, blue upon extrusion thereof gradually became white showing occurrence of a microphase separation, followed by coagulation thereby enabling the extrudate to solidify in a hollow fiber form. Then, the fiber was regenerated in a 2% by weight aqueous sulfuric acid at 20°±0.1° C. and subsequently washed with water, followed by drying. The resulting hollow fiber had an annular cross-section, and had an outside diameter of 305 μm, a wall thickness (d) of 30 μm and an inside diameter of 245 μm. The in-a-plane porosity (Pre) in every plane perpendicular to a radial direction of the annular cross-section of the hollow fiber was measured and plotted against the value of the distance of the plane from the inner wall surface divided by the wall thickness of the hollow fiber to obtain Curve B of FIG. 5. The minimum value of Pre (in this case, it was also the lowest value) was 23%, while the Pre's in the inner and outer wall surfaces of the hollow fiber were both about 60%. As a result of the observation of a frozen fracture surface (obtained by freezing the fiber in liquid nitrogen and breaking it in the same) of the hollow fiber by means of a scanning electron microscope it was confirmed that the hollow fiber of the present invention had an average particle diameter ($2S_2$) of 0.50 μm. Further, as a result of the observation of planes parallel to the membrane surfaces of the hollow fiber by means of a scanning electron microscope it was confirmed that the hollow fiber of the present invention had a layer structure.

The porous polymer wall of the hollow fiber had a pore structure in which the in-a-plane average pore diameter continuously varied between the inner wall surface and the outer wall surface so that with a distance from the inner wall surface, the in-a-plane average pore diameter alternately decreased and increased twice, thereby experiencing occurrences of a minimum value ($D_2$), a maximum value ($D_3$) and a minimum value ($D_4$) in this order. The in-a-plane average pore diameter ($D_1$) in the inner wall surface was 0.61 μm, and the in-a-plane average pore diameter ($D_5$) in the outer wall surface was 0.60 μm. $D_3$ was 0.15 μm, $D_3/D_2$ was 1.32 and $D_3/D_4$ was 1.31. The bulk porosity of the hollow fiber was 48.2%. The apparent average pore diameter ($2\bar{r}_f$) was 50 nm. With respect to this hollow fiber, a filtration test was conducted using as a model substance of a virus a 5% by weight aqueous albumin solution containing colloidal silica particles (Cataloi® S180P manufactured and sold by Catalysts and Chemicals Industries Company limited, Japan) having a particle size of 70 to 90 nm. The filtration test albumin solution in the hollow fiber at a transmembrane pressure of 200 mmHg. The removal percentage (X) of the colloidal silica particles by the hollow fiber was calculated from the ratio of the silica concentration (A) of the filtrate to that (B) of the filtrand, which concentrations were determined in terms of Si concentration by atomic absorption spectroscopy, according to the formula $X = (131 A/B) \times 100$. The results obtained are shown in Table 1. Further, the filtrate was sprayed over a mesh for electron microscope which was coated with carbon, and then the existence of particles on the mesh was examined by means of an electron microscope. As a result, complete removal of the colloidal silica particles was confirmed. The permeability of albumin was about 98% as measured by liquid chromatography.

EXAMPLE 2

Cellulose linter having a viscosity average molecular weight of $2.00 \times 10^5$ was dissolved in the same cuprammonium solution as employed in Example 1 so that the concentration of the cellulose linter in the resulting cellulose linter solution became 8.0% by weight. The cellulose linter solution was filtered, followed by degassing, thereby to obtain a spinning solution. From this spinning solution, a regenerated cellulose porous hollow fiber membrane was obtained under substantially the same conditions as in Example 1. The porous polymer wall of the hollow fiber had substantially the same pore structure as described in Example 1. With respect to the particulars of the pore structure of the hollow fiber, $D_1$ was 0.325 μm; $D_5$ was 0.310 μm; $D_3$ was 0.092 μm; $D_3/D_2$ was 1.40; and $D_3/D_4$ was 1.38. The in-a-plane porosities in the inner and outer wall surfaces of the hollow fiber were 54% and 56%, respectively. The lowest value of the in-a-plane porosities in ten planes taken at equidistance which planes are perpendicular to a radial direction of the annular cross-section of the hollow fibers was 17.5% and the bulk porosity was 45.0%. The apparent average pore diameter ($2\bar{r}_f$) was 20 nm.

With respect to this hollow fiber, a filtration test was conducted in substantially the same manner as in Example 1, except that use was made of colloidal silica particles (Cataloid ® SI45P manufactured and sold by Catalists and Chemicals Industries Company Limited, Japan) having a particle diameter of 35–55 nm. The results of the filtration test are shown in Table 1. The albumin permeability as measured by liquid chromatography was about 98%.

Moreover, using the above-obtained hollow fiber, a virus removal test was conducted with respect to the plasma derived from hepatitis B virus positive blood which plasma had a total protein concentration of 5.9% and a relative concentration of hepatitis B virus in terms of DNA of 1000 units. That is, the plasma was subjected to perpendicular filtration in which the plasma was fed into the hollow fiber at its one end, while the other end of the hollow fiber was closed, at a trans-membrane pressure of 100 mmHg. The filtration rate was 0.030 l/m² hr mmHg. The relative concentration of the hepatitis B virus in the filtrate in terms of DNA was evaluated by the hybridization method using an isotope-labeled cDNA coding for hepatitis B virus. The relative concentration was below the detection limit value, thereby enabling complete removal of the virus from the plasma to be confirmed. Further, the permeability of the total proteins as measured by liquid chromatography was 90%.

COMPARATIVE EXAMPLE

In the weight proportions as indicated in Table 2, a cellulose diacetate having a degree of acetylation of 54.2% and a polymerization degree of 190 was dissolved in a mixed solvent comprised of acetone and methanol in a weight ratio of 5/1 containing $CaCl_2$ $2H_2O$ and cyclohexanol, thereby to obtain a spinning solution. Under the spinning conditions as indicated in Table 2, a hollow fiber was spun. The in-a-plane porosities in the inner and outer wall surfaces of the hollow fiber were 28% and 15%, respectively, and the in-a-plane porosities within the wall of the hollow fiber were 20% or more. An in-a-plane porosity decrease from 20% to 15% was observed in the vicinity of the outer wall surface within the wall. The in-a-plane average pore diameters in the inner wall surface and the outer wall surface of the hollow fiber were 0.52 μm and 0.54 μm, respectively. The in-a-plane porosities within the wall of the hollow fiber had no minimum value but a maximum value, which was 0.60 μm. The apparent average pore diameter ($2\bar{r}_f$) was 35 nm. With respect to this hollow fiber, a filtration test using the same colloidal silica containing aqueous albumin solution as used in Example 2 was conducted in substantially the same manner as in Example 2. The results are shown in Table 1.

TABLE 1

| | Particle Size of Colloidal Silica (nm) | Removal Percentage of Colloidal Silica (%) | Filtration Rate (l/m² hr mmHg) |
|---|---|---|---|
| Example 1 | 70–90 | 99.99 or more | 0.523 |

TABLE 1-continued

| | Particle Size of Colloidal Silica (nm) | Removal Percentage of Colloidal Silica (%) | Filtration Rate (l/m² hr mmHg) |
|---|---|---|---|
| Example 2 | 35–55 | 99.99 or more | 0.035 |
| Comparative Example | 35–55 | 90 | 0.025 |

TABLE 2

| Composition of Spinning Solution | | Spinning Conditions | |
|---|---|---|---|
| Cellulose | 45 g | Spinneret | |
| diacetate | 45 g | Orifice Diameter | 1.5 mm |
| | | Injection-tube Outside Diameter | 0.5 mm |
| Acetone/ | | | |
| Methanol | 150 g | Delivery Rate of | 4.3 ml/min |
| $CaCl_2$ $2H_2O$ | 25 g | Temperature of | 30° C. |
| Cylcohexanol | 130 g | Spinning Solution | |
| | | Composition of Injection Liquid | Aqueous Methanol Solution of 50% by Volume (25° C.) |
| | | Delivery Rate of Injection Liquid | 2.0 ml/min |
| | | Composition of Coagulating Bath | Aqueous Methanol Solution of 50% by Volume (25° C.) |
| | | Temperature of Coagulating Bath | 25° C. |
| | | Distance between the spinneret orifice and the surface of the coagulating bath | 100 mm |
| | | Reel-up Velocity | 15.4 m/min |

What is claimed is:

1. A porous hollow fiber membrane comprising structure enabling essentially complete removal of a virus from a solution containing a virus at commercially acceptable filtration rates, including a porous polymer wall having a substantially annular cross-section and a hollow space defined by the inner wall surface of said porous polymer wall which hollow space extends in the longitudinal direction of said porous polymer wall, said porous polymer wall having pores which form through-passages passing from the inner wall surface to the outer wall surface of said polymer wall, and wherein the inner and outer wall surfaces of said porous polymer wall have an in-a-plane average pore diameter of 0.01 to 10 μm, said in-a-plane average pore diameter being an average pore diameter as measured in a plane perpendicular to a radial direction of said annular cross-section, and said porous polymer wall has an in-a-plane porosity of not less than 10% measured in every plane perpendicular to a radial direction of said annular cross-section, said in-a-plane porosity varying continuously between said inner wall surface and said outer wall surface, wherein said in-a-plane porosity increases in the vicinity of each of said inner and outer wall surfaces and exhibits at least one minimum value between said inner and outer wall surfaces, said in-a-plane porosity at each of said inner and outer wall surfaces being at least 1.5 times the lowest value of the in-a-plane porosity within said porous polymer wall.

2. The porous hollow fiber membrane according to claim 1, wherein said porous polymer wall has a pore structure in which said in-a-plane average pore diameter varies continuously between said inner wall surface and said outer wall surface so that from said inner wall surface, said in-a-plane average pore diameter alternately decreases and increases at least two times, thereby experiencing occurrences of at least a minimum value, a maximum value and a minimum value in this order in the continuous variation of the in-a-plane average pore diameter between said inner and outer wall surfaces, said in-a-plane average pore diameter increasing in the vicinity of said outer wall surface.

3. The porous hollow fiber membrane according to any of claims 1 and 2, wherein said porous polymer wall has a multi-layer structure having a plurality of layers stacked in the thicknesswise direction of said polymer wall.

4. The porous hollow fiber membrane according to any of claims 1 to 3, wherein said polymer is selected from the group consisting of homopolymers and copolymers of acrylonitrile, sulfone, vinylidene chloride, vinyl chloride, vinyl acetate, methyl methacrylate, urethane, styrene and vinyl alcohol; polytrifluorochloroethylene; polytetrafluoroethylene; polyolefins; polyamides; polyesters; cellulose acetate, cellulose nitrate, cellulose butyrate and cellulose acetate butyrate; regenerated cellulose; and cellulose and mucopolysaccharides.

5. The porous hollow fiber membrane according to any of claims 1 to 4, wherein said polymer is a hydrophilic polymer.

6. The porous hollow fiber membrane according to claim 5, wherein said hydrophilic polymer is regenerated cellulose.

7. The porous hollow fiber membrane according to any of claims 2 to 6, wherein said porous polymer wall has a wall thickness of 10 to 200 $\mu$m and a bulk porosity of 30 to 75%, and the maximum value of the in-a-plane average pore diameter is not larger than 10 times the minimum value of the in-a-plane average pore diameter.

8. The porous hollow fiber membrane according to any of claims 1 to 7, wherein the ratio of the minimum value of the in-a-plane porosity (%) to the wall thickness ($\mu$m) of said porous polymer wall is in the range of from 0.05 to 2.

9. The porous hollow fiber membrane according to claim any of claims 1 to 8, wherein said in-a-plane porosity at each of said inner and outer wall surfaces is at least twice the lowest value of the in-a-plane porosity within said porous polymer wall.

* * * * *